US011197793B2

(12) United States Patent
Refsnæs et al.

(10) Patent No.: US 11,197,793 B2
(45) Date of Patent: Dec. 14, 2021

(54) MONITORING METHODS FOR MEDICAL BEDS

(71) Applicant: ABLY MEDICAL AS, Ålesund (NO)

(72) Inventors: Jørn Refsnæs, Ålesund (NO); Arve Voldsund, Leinøy (NO); Cato Alexander Bjørkli, Hvalstad (NO); Leila Yousif Circhirillo, Oslo (NO); Kjell Are Furnes, Nesoddtangen (NO)

(73) Assignee: Ably Medical AS, Ålesund (NO)

( * ) Notice: Subject to any disclaimer, the term of this patent is extended or adjusted under 35 U.S.C. 154(b) by 288 days.

(21) Appl. No.: 16/347,273

(22) PCT Filed: Oct. 24, 2017

(86) PCT No.: PCT/IB2017/056595
§ 371 (c)(1),
(2) Date: May 3, 2019

(87) PCT Pub. No.: WO2018/083567
PCT Pub. Date: May 11, 2018

(65) Prior Publication Data
US 2019/0274905 A1    Sep. 12, 2019

(30) Foreign Application Priority Data

Nov. 4, 2016  (GB) ...................................... 1618658
Apr. 4, 2017  (GB) ...................................... 1705426

(51) Int. Cl.
*A61G 7/015*        (2006.01)
*G16H 50/30*        (2018.01)
(Continued)

(52) U.S. Cl.
CPC ............ *A61G 7/015* (2013.01); *A61B 5/1036* (2013.01); *A61B 5/11* (2013.01); *A61B 5/1113* (2013.01);
(Continued)

(58) Field of Classification Search
CPC ........ A61G 7/015; A61G 7/00; A61B 5/1036; A61B 5/11; A61B 5/1113; A61B 5/1114;
(Continued)

(56) References Cited

U.S. PATENT DOCUMENTS 57,560 A    8/1866  Patton
86,120 A *  1/1869  Almond ............... A47C 23/064
                                                    5/191
(Continued)

FOREIGN PATENT DOCUMENTS

CN    101252906 A    8/2008
CN    201436920 U    4/2010
(Continued)

OTHER PUBLICATIONS

International Search Report and Written Opinion dated Jan. 18, 2018 in connection with PCT/IB2017/056594, 9 pages.
(Continued)

*Primary Examiner* — Fredrick C Conley
(74) *Attorney, Agent, or Firm* — Dorsey & Whitney LLP

(57) ABSTRACT

There is described methods of monitoring a patient on a bed. An exemplary method includes receiving one or more sensory outputs from sensors associated with the bed, analysing the one or more sensory outputs and determining a plurality of features of the patient therefrom, and receiving the plurality of patient features and determining a health assessment by inputting the patient features into a statistical model.

19 Claims, 3 Drawing Sheets

(51) Int. Cl.
    *A61B 5/11*     (2006.01)
    *A61B 5/00*     (2006.01)
    *G16H 20/30*     (2018.01)
    *A61B 5/103*     (2006.01)
    *A61G 7/05*     (2006.01)
    *A61G 7/018*     (2006.01)
    *A61G 7/057*     (2006.01)

(52) U.S. Cl.
    CPC ........... *A61B 5/6891* (2013.01); *G16H 20/30* (2018.01); *G16H 50/30* (2018.01); *A61G 7/018* (2013.01); *A61G 7/057* (2013.01); *A61G 7/0524* (2016.11); *A61G 2203/30* (2013.01); *A61G 2203/34* (2013.01); *A61G 2203/36* (2013.01); *A61G 2203/44* (2013.01); *A61G 2203/46* (2013.01)

(58) Field of Classification Search
    CPC ..... A61B 5/1116; A61B 5/1117; A61B 5/1118
    See application file for complete search history.

(56) References Cited

U.S. PATENT DOCUMENTS

| | | | |
|---|---|---|---|
| 643,208 | A | 2/1900 | Schmidt |
| 3,380,088 | A | 4/1968 | D'Adesky |
| 3,716,875 | A | 2/1973 | Fehr |
| 5,448,789 | A | 9/1995 | Shirai |
| 5,926,877 | A | 7/1999 | Lin |
| 6,877,816 | B1 | 4/2005 | Farmont |
| 9,788,800 | B2 | 10/2017 | Mayoras, Jr. |
| 10,675,755 | B2 | 6/2020 | Sinibaldi et al. |
| 2005/0172405 | A1 | 8/2005 | Menkedick et al. |
| 2008/0147442 | A1 | 6/2008 | Warner et al. |
| 2010/0080431 | A1* | 4/2010 | Datema ............ A61B 6/04 382/131 |
| 2010/0094139 | A1* | 4/2010 | Brauers ............ A61B 5/0816 600/484 |
| 2011/0295065 | A1 | 12/2011 | Gurusamy et al. |
| 2012/0259248 | A1 | 10/2012 | Receveur |
| 2013/0090763 | A1 | 4/2013 | Simaan et al. |
| 2013/0205501 | A1 | 8/2013 | Robertson et al. |
| 2014/0289962 | A1 | 10/2014 | Watkins |
| 2017/0252260 | A1 | 9/2017 | Gummin et al. |
| 2019/0274906 | A1 | 9/2019 | Refsnæs et al. |

FOREIGN PATENT DOCUMENTS

| | | |
|---|---|---|
| CN | 102697615 A | 10/2012 |
| CN | 203954044 U | 11/2014 |
| DE | 202015103036 U1 | 10/2016 |
| EP | 0608635 A1 | 8/1994 |
| EP | 2392304 A1 | 12/2011 |
| GB | 2313540 A | 12/1997 |
| GB | 2319851 A | 6/1998 |
| JP | S57-085280 U | 5/1982 |
| JP | H0650630 U | 7/1994 |
| JP | H1043008 A | 2/1998 |
| JP | 2001293037 A | 10/2001 |
| JP | 2010511149 A | 4/2010 |
| JP | 2010519948 A | 6/2010 |
| JP | 2015522379 A | 8/2015 |
| TW | 333044 U | 6/1998 |
| WO | 2008055173 A2 | 5/2008 |
| WO | 2009135081 A2 | 11/2009 |
| WO | 2014015320 A1 | 1/2014 |
| WO | 2015087204 A1 | 6/2015 |

OTHER PUBLICATIONS

International Search Report and Written Opinion dated Jan. 18, 2018 in connection with PCT/IB2017/056595, 12 pages.

First Office Action dated Oct. 27, 2020 in connection with Chinese patent application No. 201780067314.5, 20 pages including English translation.

Communication dated Jul. 27, 2020 in connection with European patent application No. 17794427.9, 5 pages.

Office Action dated Sep. 21, 2021 in connection with Japanese patent application No. 2019-546112, 11 pages including English translation.

* cited by examiner

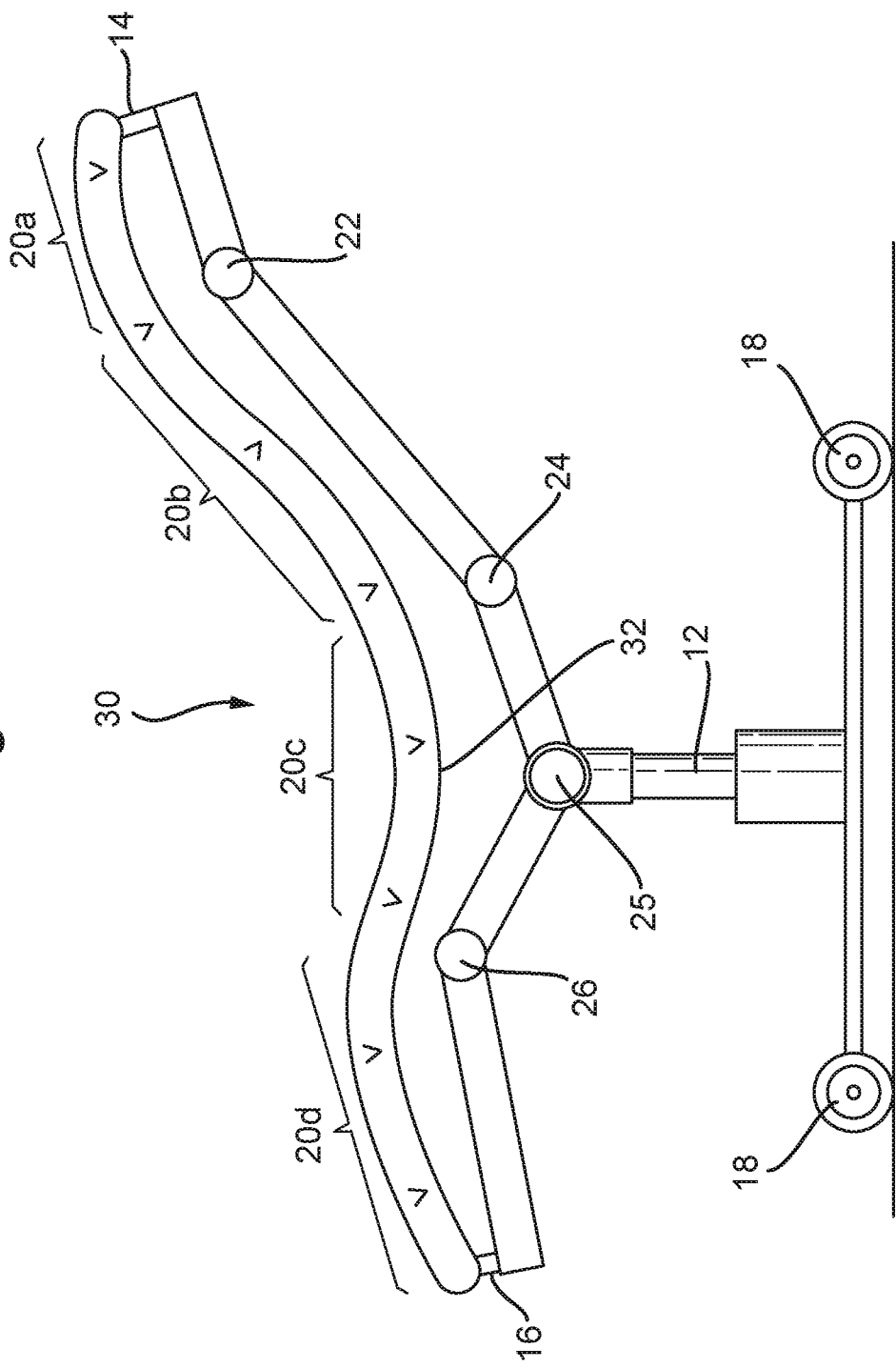

MONITORING METHODS FOR MEDICAL BEDS

FIELD OF THE INVENTION

The present invention relates generally to technologies, methods and apparatus for and associated with beds for use in a medical or therapeutic environment such as a hospital. In various aspects and embodiments the invention relates to medical, e.g., hospital beds and, more specifically, methods associated with the monitoring of patients resting on such beds, especially in terms of their comfort and movement.

BACKGROUND

Various methods exist for monitoring patients as they rest on a bed. A large number of sensors are known that can be operatively connected to a patient in order to monitor characteristics such as pulse rate, blood pressure, respiratory rate, arterial line, temperature, brain pressures and a number of other characteristics.

Typically, such characteristics are monitored individually, or in some cases by a combined monitor. For example, in the case of blood pressure and pulse rate, a bedside cardiac monitor may track and display vital signs, and output various alerts if the vital signs follow predefined patterns that indicate that the patient is in trouble.

The sensors and monitors currently available typically do not combine different types of characteristics. For example, cardiac monitors do not keep track of a patient's temperature, and are not configured to combine the vital sign information with other information about the patient. Moreover, alerts are typically based on only a single variable (e.g., pulse rate) and do not combine a number of different variables.

It is therefore desired to provide improved methods of monitoring patients as they rest on a bed, for example a hospital bed, and to combine such methods with new types of bed that allow such monitoring to be carried out more efficiently.

SUMMARY

An aspect of the present invention relates to a method of monitoring a person on a bed, comprising the steps of:

receiving one or more, e.g., a plurality of sensory outputs from sensors associated with the bed;

analysing the one or more (e.g., a plurality of) sensory outputs and determining one or more (e.g., a plurality of) features of the patient therefrom;

receiving the one or more (e.g., a plurality of) patient features and determining a health assessment by inputting the patient features into a statistical model; and optionally determining one or more corrective actions based on the health assessment.

The methods disclosed herein are, in the broadest aspects, seen as improvements over conventional methods of monitoring a person on a bed. By using a statistical model to determine a health assessment, as described herein, using various sensory outputs which are analysed to provide health features, which themselves are used as inputs into the statistical model, improves the manner in which sensory outputs may be used to produce a health assessment.

Some or all of the sensors may be within the bed (e.g., a support structure thereof), for example the sensors (e.g., pressure sensors or any of the other types of sensors referred to herein) may be located in an array across the bed such that different portions of the patient can be monitored. In addition, or alternatively, some or all of the sensors may be located remotely from the bed, and may be configured to sense characteristics of the patient using, e.g., remote sensing techniques.

The corrective actions may include any care action suitable for the situation at hand. The corrective actions may include, but are not limited to, adjusting the bed (e.g., automatically), opening a communication link between the patient and a caregiver, and sounding an alert or outputting a flag or notification that a particular event associated with the health assessment has occurred.

Any or all of the method steps may be carried out using a control system or monitoring apparatus, for example a computer. The control system or monitoring apparatus may be located adjacent to the bed, or even located within the bed or form part of it. In some embodiments, as described in more detail below, some of the method steps may be carried out using an apparatus adjacent to the bed, whilst the other steps may be carried out using a central or remote apparatus.

The one or more patient features may comprise a flag or notification that the value of one of the one or more sensory outputs, or a value derived from one of the one or more sensory outputs, exceeds one or more predefined threshold values. The one or more patient features may comprise a flag or notification that the value of a trend or rate of change of one or the one or more sensory outputs exceeds one or more predefined threshold values. Such patient features may be useful, for example, in detecting sharp increases or decreases in sensory outputs, and their effect in a wider context on the health assessment.

The one or more patient features may comprise a flag or notification that the value of one of the one or more sensory outputs, or a value derived from one of the one or more sensory outputs has not substantially changed or fallen outside of a predefined range for a predefined amount of time. This may be used to indicate a lack of movement of the patient, which can be useful in detecting bedsores or pressure ulcers.

A plurality of patient features may be input into the statistical model in order to determine a health assessment, for example at least 3, 4, 5 or 10 patient features may be input into the statistical model in order to determine a health assessment.

A "health assessment" may be seen as a high level outcome based on the analysis of a plurality of health features input into the statistical model.

The statistical model may comprise a Bayesian network, Bayes network, belief network, Bayes(ian) model or probabilistic directed acyclic graphical model, and may be represented or representable by a probabilistic graphical model that represents a set of random variables and their conditional dependencies, e.g., via a directed acyclic graph (DAG).

The statistical model may comprise one or more of a causal network, a Bayesian inference algorithm, a Bayesian Belief Network ("BBN") and a Fuzzy Belief Network ("FBN").

The statistical model may represent a probabilistic relationship between the one or more patient features and one or more events, outcomes or situations (e.g., possible health assessments).

The step of determining a health assessment may comprise inputting the one or more patient features into a conditional probability table. The health assessment may be a flag or notification that the patient is about to fall off the bed, or that the patient is likely to be developing (or has developed) a bedsore or pressure ulcer, e.g., in a certain location.

The one or more sensory outputs may include sensory outputs from an array of pressure sensors located across the bed, and the one or more patient features may include a flag or notification that the patient is close to and/or moving to the side of the bed, and/or a flag or notification that the patient has not moved for a predetermined period of time.

The bed may comprise a support structure configured to support a body in use. The support structure may comprise a plurality of resilient members (e.g., springs) that each extend lengthwise along the bed from an upper end of the bed to a lower end of the bed, and the array of pressure sensors may be connected to the plurality of resilient members.

The bed may be separated into one or more movable portions, and the one or more corrective actions may comprise a command for a control system to move one of the one or more movable portions to prevent the patient falling off the bed, or to prevent/relieve a bedsore or pressure ulcer.

The method may further comprise noting if a particular health assessment occurs repeatedly, recording any common patient features that are received at each occurrence of the health assessment, and updating or improving the statistical model associated with the health assessment using the common patient features.

The updating may comprise amending a threshold value (e.g., one of the predefined threshold values referred to above) or other value (e.g., the predefined range or predefined amount of time referred to above) associated with one of the patient features.

An aspect of the present invention, which may be claimed independently, relates to a method of monitoring a patient on a bed, comprising:

(i) receiving a plurality of sensory outputs from sensors associated with the bed;

(ii) analysing the plurality of sensory outputs and determining a plurality of features of the patient therefrom;

(iii) receiving the plurality of patient features and recording the time at which the patient features occur;

(iv) noting that an event, outcome or situation relating to the patient has occurred;

(v) repeating steps (i)-(iv) and noting if a particular event, outcome or situation occurs repeatedly, and recording any common patient features that are received at each occurrence of the particular event, outcome or situation.

The particular event, outcome or situation may be that the patient falls off the bed, or is about to fall off the bed.

The method may further comprise determining a statistical model that uses the common patient features as inputs, and outputs a probability that the particular event, outcome or situation will occur.

The method may further comprise continuing to receive the plurality of patient features and continuously inputting these into the statistical model, and outputting a flag or notification if the probability that the particular event, outcome or situation will occur exceeds a predefined threshold.

The method may further comprise determining one or more corrective actions to prevent the particular event, outcome or situation from occurring.

The various method steps or functions of any aspects or embodiments of the present invention (including those defined above and elsewhere herein) can be carried out in any desired and suitable manner. For example, the method steps or functions of the present invention can be implemented in hardware or software, as desired. Thus, for example, unless otherwise indicated, the various method steps, functional elements, stages, and "means" of the invention may comprise a suitable processor or processors, controller or controllers, functional units, circuitry, processing logic, microprocessor arrangements, etc., that are operable to perform the various functions, etc., such as appropriately dedicated hardware elements and/or programmable hardware elements that can be programmed to operate in the desired manner.

It should also be noted here that, as will be appreciated by those skilled in the art, the various method steps or functions, etc., of the present invention may be duplicated and/or carried out in parallel on a given processor. Equally, the various processing stages may share processing circuitry, etc., if desired.

It will also be appreciated by those skilled in the art that all of the described aspects and embodiments of the present invention can, and preferably do, include, as appropriate, any one or more or all of the preferred and optional features described herein.

The methods in accordance with the present invention may be implemented at least partially using software e.g. computer programs. It will thus be seen that when viewed from further aspects the present invention provides computer software specifically adapted to carry out the methods herein described when installed on data processing means, a computer program element comprising computer software code portions for performing the methods herein described when the program element is run on data processing means, and a computer program comprising code means adapted to perform all the steps of a method or of the methods herein described when the program is run on a data processing system. The data processor may be a microprocessor system, a programmable FPGA (field programmable gate array), etc.

The invention also extends to a computer software carrier comprising such software which when used to operate a graphics processor, renderer or microprocessor system comprising data processing means causes in conjunction with said data processing means said processor, renderer or system to carry out the steps of the methods of the present invention. Such a computer software carrier could be a physical storage medium such as a ROM chip, CD ROM, RAM, flash memory, or disk, or could be a signal such as an electronic signal over wires, an optical signal or a radio signal such as to a satellite or the like.

It will further be appreciated that not all steps of the methods of the invention need be carried out by computer software and thus from a further broad aspect the present invention provides computer software and such software installed on a computer software carrier for carrying out at least one of the steps of the methods set out herein.

The present invention may accordingly suitably be embodied as a computer program product for use with a computer system. Such an implementation may comprise a series of computer readable instructions either fixed on a tangible, non-transitory medium, such as a computer readable medium, for example, diskette, CD ROM, ROM, RAM, flash memory, or hard disk. It could also comprise a series of computer readable instructions transmittable to a computer system, via a modem or other interface device, over either a tangible medium, including but not limited to optical or analogue communications lines, or intangibly using wireless techniques, including but not limited to microwave, infrared or other transmission techniques. The series of computer readable instructions embodies all or part of the functionality previously described herein.

Those skilled in the art will appreciate that such computer readable instructions can be written in a number of programming languages for use with many computer architectures or operating systems. Further, such instructions may be stored using any memory technology, present or future, including but not limited to, semiconductor, magnetic, or optical, or transmitted using any communications technology, present or future, including but not limited to optical, infrared, or microwave. It is contemplated that such a computer program product may be distributed as a removable medium with accompanying printed or electronic documentation, for example, shrink wrapped software, preloaded with a computer system, for example, on a system ROM or fixed disk, or distributed from a server or electronic bulletin board over a network, for example, the Internet or World Wide Web.

BRIEF DESCRIPTION OF THE DRAWINGS

Various embodiments will now be described, by way of example only, and with reference to the accompanying drawings in which:

FIG. 1 shows a bed in accordance with one embodiment of this invention; and

DETAILED DESCRIPTION

Figure 2A:
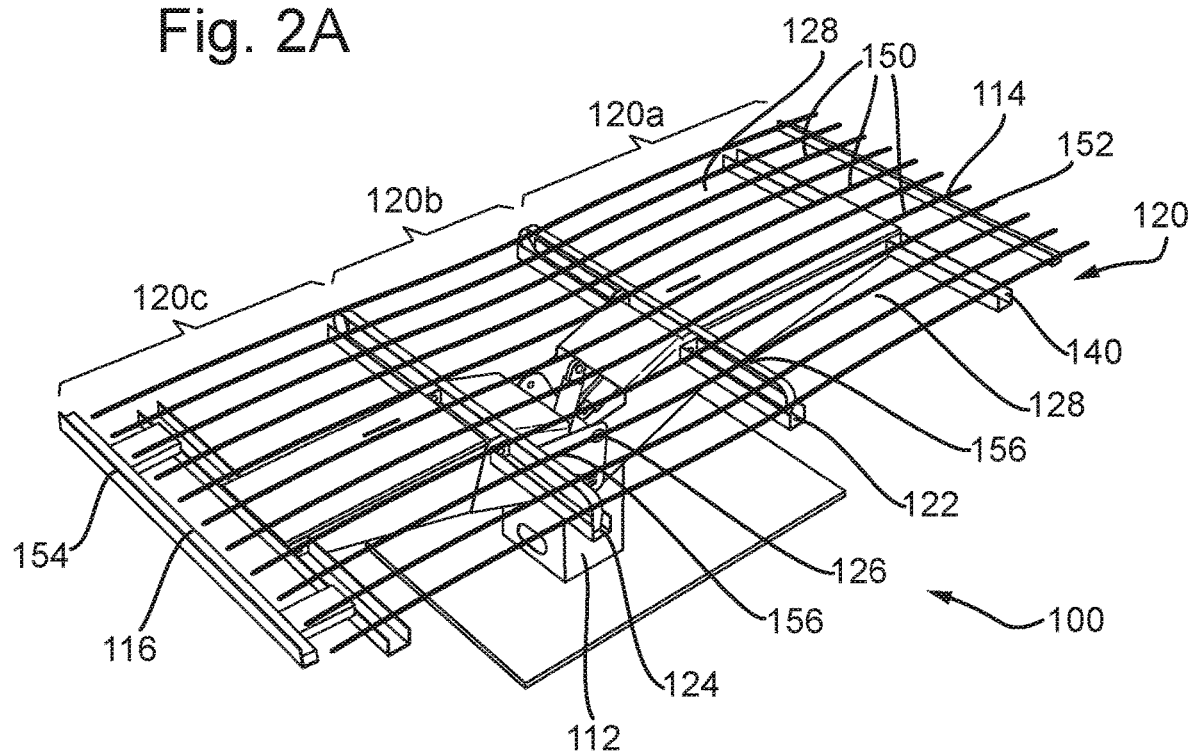
FIGS. 2A and 2B show a bed in accordance with another embodiment of this invention.

Various aspects of the present invention will be described below, which broadly relate to methods of monitoring a person (or patient) as they rest on a bed, for example a medical bed, such as a hospital bed. Examples of such a bed are described below and in relation to FIGS. 1 and 2A-2B. The methods involve improvements in the way a patient may be monitored. For example, the status or output of various types of sensor may be combined and a patient feature may be output therefrom.

A "patient feature" as defined herein may refer to a feature of the patient that is determined from analysing one or more sensory outputs. Such features may not be obtainable through direct sensory observation. Rather, although the patient features may be determined from a direct sensory output, such as a temperature value from a thermometer connected to the patient or bed, it should be understood that some kind of analysis of the sensory output will take place, e.g., averaging, sampling, etc. as described in more detail below. The patient features may be in the form of a flag or notification, and may be produced using an analysis module as described herein.

Certain patient features may be defined as features of the patient that are output when the value of one or more sensory outputs, or value derived from the one or more sensory outputs exceeds one or more predefined threshold values. Other patient features may be defined as features of the patient that are output when the value of a trend or rate of change of the one or more sensory outputs exceeds one or more predefined threshold values. These patient features typically relate to abnormal situations, such as a high pulse rate, or rapidly increasing or decreasing pulse rate.

It will be appreciated, however, that certain patient features may relate to normal situations, and may be a determination from analysing one or more sensory outputs that the patient has a normal pulse rate, or a normal temperature. These patient features can also be important when assessing the overall health of the patient as described herein.

The value derived from the one or more sensory outputs may be a sampled value, for example an average value. The sampling (e.g., averaging) may be carried out by the sensor itself, or within the analysis module as part of the algorithm for determining a patient feature.

The patient features may be determined using a plurality of sensory outputs, for example a first thermometer connected to the patient's torso (or upper half of the bed) may detect an increase in temperature (e.g., the temperature may rise above a threshold), while a second thermometer connected to the patient's legs (or lower half of the bed) may detect no increase in temperature (e.g., the temperature may remain within one or more thresholds). In this case, a patient feature may be that the patient's core temperature is increasing relative to the rest of the patient.

A further example of a patient feature determined using a plurality of sensory outputs may be that the patient is moving towards the side of the bed. This may be determined from a plurality of position, motion, pressure or other suitable sensors within the bed.

A further example of a patient feature determined using a plurality of sensory outputs may be that the patient is not moving, or has not moved by more than a predefined amount for a predefined time. This may be determined from a plurality of position, motion, pressure or other suitable sensors within the bed.

The patient feature(s) may be output from the analysis module and combined with other patient features and input into an assessment module to determine a health assessment.

For example, a patient feature may be output that the patient is moving towards the side of the bed, and a separate patient feature may be output that the patient is moving erratically. These may be combined to produce an assessment that the patient is about to fall off the bed. This can lead to an alert being made to a caregiver that the patient is about to fall off the bed, allowing the caregiver to prevent this from happening. Alternatively, or additionally, an action may be taken, such as causing the bed to form a concave profile (e.g., a dip or valley), in order to prevent the patient falling off.

In a further example, a patient feature may be output that the patient has not moved by more than a predefined amount for a predefined time, and a separate patient feature may be output that the patient is awake. A further patient feature may be a location of high or maximum pressure in a region of the bed. These may be combined to produce an assessment that the patient is about to develop an uncomfortable pressure ulcer or bedsore. This can lead to an alert being made to a caregiver that the patient is about to develop or has developed a pressure ulcer or bedsore, allowing the caregiver to prevent this from happening. Alternatively, or additionally, an action may be taken, such as causing the bed to move (e.g., in the region of high or maximum pressure, or the whole bed) in order to alleviate or prevent the bedsore or pressure ulcer.

The methods disclosed herein extend to methods of learning how a harmful patient outcome was caused. The monitoring methods may be used and analysed to determine what sequence of patient features lead to a particular outcome, for example a patient falling off the bed.

In various embodiments the methods may include outputting an alert that the same sequence of patient features are occurring, so that the same harmful patient outcome can be prevented.

In various embodiments the monitoring methods used may be combined with a specific type of bed that will be described in more detail below. This type of bed allows certain monitoring methods to be used that are not possible with conventional arrangements, due to the arrangement of the bed or lack of available sensory outputs when using a conventional bed.

Furthermore, the specific type of bed may allow certain recovery actions to be made that are not possible with conventional beds (e.g., the bed may automatically form a concave profile, or make small, localised movements to relieve or prevent a pressure ulcer or bedsore), and these will be described in more detail below.

Other applications for the monitoring methods as disclosed herein are contemplated, and any application that will make use of the disclosed improvements are intended to fall within the scope of the present invention even if not explicitly stated. For example, the methods are not limited to use in a hospital environment, but could be used, e.g., in a physiotherapy clinic to aid in recovery from certain injuries, or in a therapeutic environment.

Non-medical applications are also contemplated and intended to fall within the broadest aspects of the invention as described herein. As such, references to "patient" and "caregiver" herein are not intended to limit the embodiments to medical applications, and the terms "patient" and "caregiver" are interchangeable with any terms that refer to a person that might lie on, use or operate the bed as appropriate, for example "user", "controller" or "operator". As used herein, the term "resilient" may refer to a material that is able to recoil (or spring) back into shape after bending, stretching, or being compressed.

Monitoring

Where possible hospitals will try to continuously monitor patients. For example, in intensive care units patient can be wired up to a large number of monitors (perhaps up to 25 or 30), each of which may continuously monitor a single characteristic of the patient, for example pulse rate and blood pressure. Outside of intensive care, such continuous monitoring is either unfeasible or unnecessary, and instead of continuously monitoring patients, caregivers may manually monitor and record samples of such characteristics periodically. Although this does save resources, it is not possible to know what happens between manual measurements. The present invention is aimed at improving how patients are monitored, and the quality of data or health assessments that can be produced while a patient is lying on a bed.

The aim, therefore, of the present invention is to provide a monitoring or control system that can monitor patients more often, with a high degree of accuracy, while reducing the resources required to monitor important characteristics of the patient. The aim is not to eliminate the use of manual caregivers, but to find an optimum balance between continuous monitoring and manual monitoring. This will reduce the burden on caregivers so that they can concentrate on other important tasks. For example, the methods disclosed herein (and described in more detail below) may monitor when a patient is asleep, so that a caregiver can be notified of this, which saves them time checking and allows them to carry out other important tasks.

The control system (or monitoring apparatus) may be in the form of one or more units that may be located within or adjacent to the bed, for example above it. The control system may form part of a multipurpose digital computing device, for example a computer, which may be located within, near to or remote from the bed. Each module (as described below) or unit may be located in the same, or a different location.

The control system may comprise one or more sensors (e.g., wireless sensors), and may comprise one or more computers configured to carry out steps of monitoring, including receiving data from the one or more sensors and processing this data using one or more algorithms to produce one or more patient features. The one or more patient features may be further combined or used to produce a health assessment, which itself can be used to produce a recommended action.

The architecture of the control system may include a sensor analysis module for collecting sensor data output from the one or more sensors, and processing this data to generate one or more patient features. As will be described below, the patient features may be extracted from sensory observations. For example, if a patient's pulse rate exceeds a predefined threshold, a patient feature may be generated in the form of a flag representing a high pulse rate. Other patient features may be extracted from a plurality of sensory observations.

The patient features output from the sensor analysis module may be analysed by a assessment module, which may be configured to analyse the patient features (e.g., using a suitable algorithm) and output a health assessment. The health assessment may be then be used to produce a corrective action, for example cause the bed to automatically move or sound an alert. The assessment module may only analyse patient features and/or may not receive direct sensory outputs.

It will be appreciated that this architecture can reduce the amount of data sent between the various modules. For example, the sensor analysis module may be located adjacent to the bed, and the assessment module may be located remote from the bed.

However, the analysis module does not continuously transmit data, e.g. sensor data, and instead analyses such data and only outputs patient features when necessary (e.g., periodically). The analysis module may continuously receive data from one or more sensors, and output patient features intermittently, periodically and/or, for example when one or more of the sensory outputs exceed a predefined value.

Similarly, the assessment module may be located within or adjacent to the bed as well, and may only output a health assessment, alert or other action when necessary. In either situation there is an improvement to conventional arrangements, which transmit data continuously or require manual monitoring periodically. Wth the technology disclosed herein, it is possible to strike a balance between these two extremes.

Sensors and Analysis Module

Various types of sensors may be used with the monitoring or control systems and methods as described herein. A number of these will be described below, although it will be appreciated that any suitable sensor may be incorporated into the monitoring systems and methods as desired.

The one or more sensors may comprise a weight sensor, e.g., a weighing scales operatively connected to the bed that is configured to measure the weight of the bed (including the person on the bed) as well as changes in the weight of the bed. The weight of the person lying on the bed may be calculated by subtracting the weight of the bed without the person from the weight of the bed with the person, or using any other suitable method.

The sensor analysis module may be configured to continuously monitor the weight of the bed (and/or the person on the bed). The sensor analysis module may be configured to output a patient feature (e.g., a flag or notification) if this weight deviates by more than a predetermined amount. In some embodiments, the patient feature may be sent to the control system, which could then sound an alarm and/or record the time of the deviation, and the amount by which the weight deviated.

The one or more sensors may comprise a temperature sensor. The temperature sensor may be a remote temperature sensor, such as an infrared temperature sensor. The sensor analysis module may be configured to continuously monitor the temperature of the person on the bed. Alternatively, or additionally, the sensor analysis module may output a patient feature (e.g., a flag or notification) if this temperature deviates by more than a predetermined amount, or if the rate of change of this temperature exceeds a predefined threshold value. The patient feature may be abnormal patient temperature or a rapidly changing (e.g., increasing or decreasing) patient temperature. In some embodiments, the control system could then sound an alarm and/or record the time of the deviation, and the amount by which the temperature deviated.

It will be appreciated that the patient features determined by the control system may be a more simple analysis of the sensory output, and could simply be a current or latest temperature of the patient. Such patient features may be useful in the complex health assessments described herein.

The one or more sensors may comprise a sensor or sensors configured to measure the length or height of a person on the bed. For example, one or more cameras may be placed above the bed, and may be configured to detect the top and bottom of the person's body on the bed. Alternatively, one or more position sensors may be located within the bed, and may be configured to sense the position of the top and bottom of the person's body on the bed. The control system may be configured to calculate the length of the person based on the response of the one or more cameras or other sensors, and output the length (or height) of the person as a patient feature.

The one or more sensors may comprise one or more pulse rate sensors, configured to measure the pulse rate of the person on the bed. The sensor may be a remote and/or non-contact sensor (e.g., the sensor may be placed above the bed). The pulse rate of the person on the bed may be monitored continuously by the control system (e.g., the sensor analysis module). If the pulse rate deviates by more than a predetermined amount, or if the rate of change of the pulse rate exceeds a predefined threshold value, then a patient feature (e.g., a notification) may be output by the control system, indicating an abnormal pulse rate or rapidly increasing or decreasing pulse rate.

A further patient feature determined by the sensor analysis module may be an average of the pulse rate. The average pulse rate may be determined by measuring the value output from the pulse rate sensor at predefined intervals (e.g., every 30 seconds) and calculating the average of these values, again at predefined intervals (e.g., every 5 minutes).

If the pulse rate, or average pulse rate deviates by more than a predetermined amount, or if the rate of change of the pulse rate or average pulse rate exceeds a predefined threshold value, then a patient feature (e.g., a notification) may be output by the control system, indicating an abnormal pulse rate or average pulse rate, or rapidly changing (e.g., increasing or decreasing) pulse rate or average pulse rate.

The control system may also relay the notifications and/or alarms, for example to a central server at a hospital for further processing, monitoring or recording.

The one or more sensors may comprise a sensor configured to measure the skin colour or tone of the person on the bed. The colour sensor may be a remote and/or non-contact sensor. The skin colour or tone of the person on the bed may be monitored continuously by the control system (e.g., the sensor analysis module). If the skin colour or tone changes significantly, or one or more predetermined colour hues are detected, then a patient feature (e.g., a notification) may be output by the control system indicating an abnormal skin tone. The control system could then sound an alarm and/or record the time of the abnormal skin tone, and the amount by which the skin tone changed. The control system may also relay the notifications and/or alarms, for example to a central server at a hospital for further processing, monitoring or recording.

The one or more sensors may comprise one or more motion detectors. The motion detectors may be configured to detect relatively large movements of the person on the bed (e.g., of the order of 10 cm or greater). The sensor analysis module may be configured to output a patient feature (e.g., raise a flag or notification) if the movements exceed a predefined threshold (e.g., are of the order of 10 cm or greater). This may indicate that the person is having difficulty, e.g., due to a major seizure.

The sensor analysis module may, additionally or alternatively, be configured to detect a lack of movement. For example, if no movement is detected greater than a predefined amount (e.g., 10 cm) for a predefined time (e.g., 5 minutes, 10 minutes, 30 minutes, 1 hour or more), the sensor analysis module may be configured to output one or more patient features (e.g., raise a flag or notification) to indicate the same. As discussed herein, these patient features may be used to determine that the patient is developing, or has developed a bedsore or pressure ulcer.

For example, an algorithm may be used to predict if the person is about to fall off the bed (i.e., before it happens), and a notification could be sent and/or an alarm sounded if this is predicted. In some embodiments, for example those involving a bed having movable portions, some portions of the bed may move automatically in response to the prediction, to prevent the person falling off the bed. This will be described in more detail below.

Alternatively, or additionally, one or more of the motion detectors may be configured to detect relatively small movements (e.g., of the order of less than 10 cm) of the person on the bed, which typically indicate discomfort and uneasiness. These relatively small movements may be monitored by the sensor analysis module over time. One or more algorithms could be used to predict whether the person on the bed is in a serious amount of discomfort (e.g., due to bedsores, or a minor seizure), and a patient feature (e.g., a flag or notification) indicating such discomfort could be output if this is predicted. In some embodiments, for example those involving a bed having movable portions, some portions of the bed may move automatically in response to the prediction, to prevent the person experiencing a serious amount of discomfort (e.g., a bedsore).

A plurality of motion detectors and/or other motion sensors (e.g., pressure sensors) may be mounted at various locations on the bed. For example, when using a bed having a plurality of longitudinal springs as discussed below, one or more of such detectors may be located on each spring. The sensor analysis module may be configured to receive sensory outputs from each of the detectors and determine or detect particular movement patterns therefrom. The movement patterns may be output as a patient feature, and may be that the patient is moving quickly towards the side of the bed (e.g., about to fall off), or that the patient is exhibiting movement similar to that of a seizure.

The one or more sensors may comprise one or more sound sensors. The sound sensors may be located, for example, in one or more tubes that extend into the body of a person on the bed (i.e., an intubated person). Alternatively, or additionally the sound sensors may be located in the bed, for example in the mattress to detect noises from a person lying on the bed (e.g., breathing, or bowel movements).

The sensor analysis module may be configured to monitor the sound in the tubes, and/or in the bed using the one or more sound sensors. The sensor analysis module may be configured to detect specific sounds in the tubes and/or in the bed, such as sounds that indicate discomfort or problems (e.g., mucus in the tubes, or breathing or bowel problems), and output a patient feature (e.g., a flag or notification) indicating such discomfort if these sounds are detected. The control system may be configured to detect specific sound waves (e.g., specific frequencies) and sound an alarm and/or send a notification if such waves are detected. The control system may also relay the notifications and/or alarms, for example to a central server at a hospital for further processing, monitoring or recording.

The one or more sensors may comprise a respiratory sensor configured to measure or detect the respiration of a person on the bed. The respiratory sensor may be a remote sensor, for example an impulse radar sensor, and may be used by the sensor analysis module to detect and monitor breathing rates and patterns. This can be combined with the motion sensors described above to output a patient feature using data from both the respiratory sensor and the motion sensor. The control system may process these data to output a patient feature indicating whether the person on the bed is sleeping. The control system may continuously (or periodically) determine whether the person on the bed is asleep (using the respiratory and motion data) and output the status of the person (e.g., "awake" or "asleep") continuously (or periodically) as a patient feature.

Any and all of the sensors described above, as well as optionally the control system may be mounted in a single housing, for example above the bed. The processing of the data output from the sensors may be carried out by the sensor analysis module (as described above) to produce the one or more patient features. If desired, these patient features (rather than all of the sensor data) may be communicated to a central computer (e.g., a hospital server), and may be communicated periodically. This can help reduce the data processing and/or storage requirements of a server configured to process or store data relating to multiple beds. For example, hospitals may struggle to build and maintain servers that can process and store large amounts of sensor data for all of the beds in the hospital. By only sending certain patient features, the requirements for the central server may be reduced.

Analysis and Assessment Module

The control system may be configured to receive multiple sensory outputs (in the form of, e.g., data streams or packets) from a plurality of different sensors, for example any or all of the sensors described above, and combine these sensory outputs for input into the sensor analysis module. The sensor analysis module may be configured to process the different sensory outputs and determine (or output) a plurality of patient features. As discussed above, each patient feature may be based on one or a combination of different sensory outputs.

The patient features output from the sensor analysis module may be input into or received by the assessment module, which may analyse the various patient features and determine one or more health assessments. Each health assessment may be based on data correlations and patterns that an algorithm within the assessment module may look for, such as the statistical model using the various patient features, e.g., a Bayesian inference algorithm, Bayesian Belief Network ("BBN") or Fuzzy Belief Network ("FBN") or causal network. Such networks are typical constructions upon which the statistical model for the health assessment may be based.

As an example, the motion sensor may be outputting sensory data in the form of a large number of small movements for a prolonged period of time, and with a high amplitude. The sensor analysis module may process this sensory data and output a patient feature indicating "prolonged uncomfortable movement". Furthermore, the temperature sensor may output sensory data comprising temperature readings that are decreasing rapidly over time. The sensor analysis module may process this data and output a patient feature indicating "temperature reducing rapidly". This combination could signify a specific health problem that needs urgent attention. As such, the assessment module may include a statistical model incorporating these patient features, and may output a health assessment if both patient features are received at the same time.

Upon receiving the health assessment, the control system may be further configured to trigger a corrective action, for example via an action module. The corrective action may be to send a message for a caregiver (e.g., nurse or doctor) to visit the person urgently. The use of an action module to determine a corrective action is optional. In the alternative, for example, each health assessment may be sent along with one or more suggested corrective actions. The control system may receive these corrective actions, and may relay them, e.g., to a caregiver, who can then choose to implement them.

In embodiments including an action module, the action module may include a database of suitable actions to be implemented in response to a given health assessment. The action module may be configured to output a suitable action based on the health assessments received from the assessment module at a given point in time. It is envisaged, for example, that a particular corrective action for one health assessment may be inappropriate if another health assessment is received at the same time and wherein that particular corrective action may have a detrimental effect on the patient in light of the other health assessment.

As an additional option, or alternative to the action module, as described above the assessment module may simply output suggested corrective actions for a caregiver to review. Certain corrective actions may be flagged as appropriate for any situation, and automatically carried out by the control system, such as those involving movement of the bed (e.g., to prevent the patient falling off the bed).

Example: Falling Off the Bed

Figure 3:
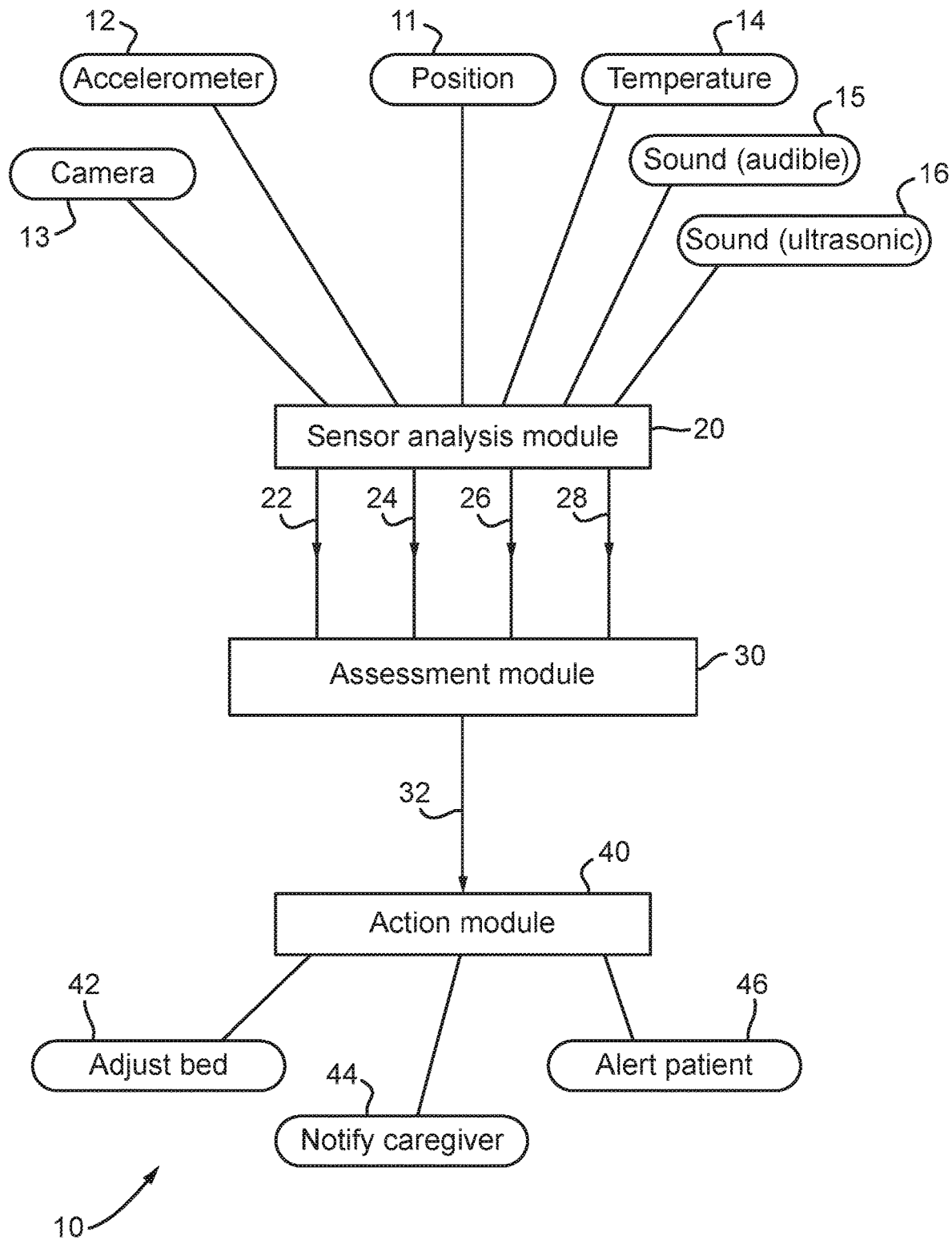
FIG. 3 shows an architecture for monitoring a person on a bed in accordance with an embodiment of the present invention.

FIG. 3 shows an architecture 10 showing schematically how the monitoring method will respond to certain sensory outputs in order to prevent a patient from falling off a bed.

The architecture 10 comprises a plurality of sensors, each configured to measure a characteristic and transmit this as a sensory output to a sensor analysis module 20.

By analysing the output of each sensor by itself, it may not be possible to predict that someone is about to fall off the bed. For example, a position sensor 11 may be configured to measure the position of a patient on the bed, and output this as a coordinate. By analysing the output of the position sensor 11 alone, one could only determine if a patient is on the bed, or if they are off it, and not make a prediction that they are about to fall off it.

In the present example, a plurality of sensors are shown, including the position sensor 11, an accelerometer 12, a camera 13, a temperature sensor 14, an audible sound sensor 15, and an ultrasound sensor 16. The output of each of the sensors may be transmitted by each sensor and received by a sensor analysis module 20, as shown schematically in FIG. 3. It may be that each sensor forms part of an array of sensors, as discussed above. For example, the position sensor 11 may form part of an array of position sensors spread uniformly across the bed. In its simplest form, only a position sensor 11 may be required to carry out a method that prevents a patient from falling off the bed, for example in conjunction with the accelerometer 12.

As discussed above, the sensor analysis module 20 is configured to receive the output of each sensor, and then output one or more patient features. For example, a first patient feature 22 may be determined from the output of the position sensor 11 and/or the camera 13, and comprise a flag or notification that the person is located at or near the edge of the bed, and/or is moving in that direction. A second patient feature 24 may be determined from the output of the accelerometer 12, and comprise a flag or notification that the acceleration of the person on the bed is above a predefined threshold. A third patient feature 26 may be determined from the output of the temperature sensor 14, and comprise a current temperature of the person on the bed. A fourth patient feature 28 may be determined from the output of the audible sound sensor 15 and/or the ultrasound sensor 16, and comprise a flag or notification of abnormal sound activity from the person on the bed.

The various patient features may be output from the sensor analysis module 20 and input into an assessment module 30, which as discussed above is configured to analyse the various patient features and determine one or more health assessments using, e.g., a statistical model as described above. In this case, the statistical model may include each of the patient features 22, 24, 26 and 28 and the assessment module may be configured to analyse each of these patient features in order to output a likelihood that the patient will fall off the bed.

For example, the assessment module 30 may determine from the first patient feature 22 that the position of the person on the bed is close to one side of the bed, and may determine from the second patient feature 24 that the patient has a high acceleration.

From this, the assessment module may output a health assessment 32 as a flag or notification of a high likelihood of the patient falling off the side of the bed. Of course, other scenarios may be envisaged that lead to this particular outcome, using any of the sensors described above.

An action module 40 may be configured to receive health assessments from the assessment module 30, including health assessment 32, and may be configured to determine one or more actions in response to the health assessments 32. For example, upon receiving a health assessment 32 that the patient is highly likely to fall off a side of the bed, the action module 40 may output a corrective action, for example a command for adjusting the bed 42 (e.g., raising the side of the bed), and/or a command to send a notification or alert to a caregiver 44, and/or a command to alert the patient 46 (e.g., by sounding an alarm adjacent to the bed).

Example: Pressure Ulcers or Bedsores

The architecture 10 of FIG. 3 may also be used to prevent or alleviate bedsores, which may be used in addition to (or alternatively to) the method described to prevent a patient from falling off a bed.

In this example, any or all of the same plurality of sensors may be used, including the position sensor 11, accelerometer 12, camera 13, temperature sensor 14, audible sound sensor 15, and ultrasound sensor 16. The output of each of the sensors may be transmitted by each sensor and received by a sensor analysis module 20, as described above. It may be that each sensor forms part of an array of sensors, as discussed above. For example, the position sensor 11 may form part of an array of position sensors spread uniformly across the bed. In its simplest form, only a position sensor 11 may be required to carry out a method that prevents or alleviates a bedsore or pressure ulcer.

As discussed above, the sensor analysis module 20 is configured to receive the output of each sensor, and then output one or more patient features. For example, a first patient feature 22 may be determined from the output of the position sensor 11 and/or the camera 13, and comprise a flag or notification that the person has not moved for a substantial (e.g., predefined) period of time. A second patient feature 24 may be determined from the output of the accelerometer 12, and comprise a flag or notification that the acceleration of the person on the bed is zero. A third patient feature 26 may be determined from the output of the temperature sensor 14, and comprise a current temperature of the person on the bed. A fourth patient feature 28 may be determined from the output of the audible sound sensor 15 and/or the ultrasound sensor 16, and comprise a flag or notification of sound activity associated with being awake or asleep, or a flag or notification that the person is awake or asleep.

The various patient features may be output from the sensor analysis module 20 and input into an assessment module 30, which as discussed above is configured to analyse the various patient features and determine one or more health assessments using, e.g., a statistical model as described above. In this case, a statistical model may include each of the patient features 22, 24, 26 and 28 and the assessment module may be configured to analyse each of these patient features in order to output a likelihood that the patient is developing or has developed a bedsore or pressure ulcer.

For example, the assessment module 30 may determine from the first patient feature 22 that the patient has not moved for a long period of time, and may determine from the fourth patient feature 28 that the patient is awake. From this, the assessment module may output a health assessment 32 as a flag or notification of a high likelihood of the patient developing, or having developed a bedsore or pressure ulcer. Of course, other scenarios may be envisaged that lead to this particular outcome, using any of the sensors described above.

An action module 40 may be configured to receive health assessments from the assessment module 30, including health assessment 32, and may be configured to determine one or more actions in response to the health assessments 32. For example, upon receiving a health assessment 32 that the patient is developing, or has developed a bedsore or pressure ulcer, the action module 40 may output a corrective action, for example a command for adjusting the bed 42 (e.g., moving the bed), and/or a command to send a notification or alert to a caregiver 44, and/or a command to alert the patient 46 (e.g., by sounding an alarm adjacent to the bed).

Learning Module

The monitoring methods and the architectures described herein may comprise a learning module, which may be configured to monitor the various patient features, health assessments and corrective actions in such a way to predict and prevent future events (e.g., harmful outcomes).

The learning module may note that a particular event has occurred, or is repeatedly occurring. For example, the patient may fall or repeatedly be falling off the bed, and/or repeatedly developing pressure ulcers. In such a situation, the learning module may record the patient features and/or health assessments that lead or led to such events, and output a statistical model of patient features and/or health assessments that indicate that the particular event will occur again. The assessment module may add this new statistical model to a database of such models, and continue to monitor the patient features and/or health assessments being output from the analysis module and assessment module such that a corrective action can be made in response to this new statistical model being satisfied. The corrective action may be a notification (e.g., to a caregiver) that the particular event is about to occur again.

The user interface may be provided so that the learning module can note that a particular event has occurred. For example, when a patient falls off the bed an operator of the learning module may input, e.g., via the user interface a new event to be monitored. If the patient falls off the bed again, then the operator may input, e.g., via the user interface that the event has happened again. The learning module may proceed as outlined above, and a statistical model may be produced that is indicative of the patient falling off the bed.

It will be appreciated that this approach could be made for any event, since the learning module does not need to know what the event is, but simply the time at which the event occurs so that the patient features and/or health assessments that led to the event can be recorded. The operator needs to know what the event is, and this can be done simply using a database incorporating the event name (e.g., input by the user interface) and the statistical model associated with that event name.

The learning module may also use the above approach to improve existing health assessments and in particular the statistical model associated with them. In one example, an event may occur that the assessment module should have predicted by outputting an associated health assessment. For example, a patient may fall off the bed without a health assessment being output that the patient was about to fall off the bed, or a pressure ulcer developed without a health assessment being output that one would develop or has developed.

The learning module may note that this event has occurred, for example by detecting from a sensory output that the patient has fallen off the bed, or by an operator inputting this information, e.g., via the user interface. The learning module may then analyse the patient features that led to the event happening, and compare these with the associated health assessment and statistical model. Some of these patient features will already be included in this statistical model. However, there may be other patient features that also are significant, but perhaps not included in the original statistical model. Alternatively, or additionally the thresholds used to produce the patient features may not match up with the value of the sensory output (or derivative thereof) at the time of the event.

The learning module may be configured to amend the statistical model such that the associated health assessment would have been determined, produced or output prior to the event happening (e.g., prior to the patient falling off the bed). For example, the learning module may include further patient features in the statistical model if these patient features are consistently present when the event occurs. The learning module may additionally, or alternatively amend the thresholds used to produce the patient features such that they match up with the values of the sensory outputs (or derivatives thereof) when the event occurs.

The Bed and Support Structure

An example of a bed 10 suitable for use in any of the aspects and embodiments of the invention described above is shown in FIG. 1. The bed 10 may comprise a bed support 12 that may be adjustable, for example telescopic such that the bed support 12 can raise and/or lower a patient lying on the bed 10 by adjusting the bed support 12. The adjustment of the bed support 12 may be provided using a motor (not shown) or, less preferably, a manual device such as a lever.

The bed 10 may comprise an upper end 14 and a lower end 16. The upper end 14 may refer to the end of the bed 10 closest to or configured to support a patient's head, while the lower end 16 may refer to the end of the bed 10 closest to or configured to support a patient's legs or feet. The bed 10 may comprise wheels 18 to allow or assist movement of the bed 10.

The bed 10 may further comprise a support structure 20 for supporting a patient and/or adapting the shape of the bed in use. The support structure 20 may comprise a plurality of sections 20a, 20b, 20c, 20d. Four sections are shown in FIG. 1 although the present invention is not limited to the use of four sections. However, use of at least three sections has been found to be convenient since the body comprises two major points of flexure while lying down, namely at the knees and waist. In the embodiment of FIG. 1 a further (optional) point of flexure is provided for the neck. This will be described in more detail below.

The support structure 20 may comprise a first section 20a which preferably supports the head of a patient lying on the bed 10. The first section 20a may be rotatable or otherwise movable (e.g., up and down) such that the head of the patient may be raised and/or lowered. A motor (not shown) may be provided to rotate or raise/lower the first section 20a, for example about a first pivot point 22. Rotation or other movement of the first section 20a may act to raise and/or lower the head of a patient lying on the bed 10.

The support structure 20 may comprise a second section 20b which preferably supports the back of a patient lying on the bed 10. The second section 20b may be rotatable or otherwise movable (e.g., up and down) such that the upper body, torso or back of the patient may be raised and/or lowered. A motor (not shown) may be provided to rotate or raise/lower the second section 20b, for example about a second pivot point 24. Rotation or other movement of the second section 20b may act to raise and/or lower the upper body, torso or back of a patient lying on the bed 10.

The second section 20b may be connected to the first section 20a at the first pivot point 22, in such a manner that the first section 20a and the second section 20b may be free to rotate or otherwise move relative to each other, for example the first section 20a may be connected to the second section 20b via a hinge.

The support structure 20 may comprise a third section 20c which preferably supports the upper legs (e.g., the portion of the body between the knees and waist) of a patient lying on the bed 10. The third section 20c may be movable such that a concave portion 30 is created at the third section 20c. To achieve this a central pivot point 25 may be located generally in the middle of the third section 20c, and the support structure may be configured such that upper and lower halves of the third section 20c (which may be separated by the central pivot point 25) can be rotated towards each other to create the concave portion 30.

The third section 20c may be configured such that the upper legs of the patient may be raised and/or lowered by rotating or otherwise moving (e.g., raising or lowering) the lower half of the third section. A motor (not shown) may be provided to rotate or otherwise move the lower half of the third section 20c, for example about the central pivot point 25. Rotation of the lower half of the third section 20c may act to raise and/or lower the legs (and specifically the upper legs) of a patient lying on the bed 10.

The third section 20c may be connected to the second section 20b at the second pivot point 24, in such a manner that the second section 20b and the third section 20c may be free to rotate or otherwise move relative to each other, for example the second section 20b may be connected to the third section 20c via a hinge.

The support structure 20 may comprise a fourth section 20d which preferably supports the lower legs (e.g., the portion of the body below the knees, including the feet) of a patient lying on the bed 10. The fourth section 20d may be rotatable or otherwise movable (e.g., up and down) such that the lower legs of the patient may be raised and/or lowered. A motor (not shown) may be provided to rotate or raise/lower the fourth section 20d, for example about a third pivot point 26. Rotation or other movement of the fourth section 20d may act to raise and/or lower the legs (and specifically the lower legs) of a patient lying on the bed 10.

The fourth section 20d may be connected to the third section 20c at the third pivot point 26, in such a manner that the third section 20c and the fourth section 20d may be free to rotate or otherwise move relative to each other, for example the third section 20c may be connected to the fourth section 20d via a hinge.

Each of the plurality of sections 20a, 20b, 20c, 20d may be rotatable or movable and may be rotatable or movable independently of one another. A common motor may be provided and may be configured to rotate or move each of the sections 20a, 20b, 20c, 20d, or a plurality of motors may be provided, for example each section of the plurality of sections 20a, 20b, 20c, 20d may have a dedicated motor configured to rotate or move its respective section.

Each of the plurality of sections 20a, 20b, 20c, 20d may be connected to an adjacent section, for example via a hinge. The support structure 20 may, in this manner, be removable or replaceable as a single unit.

The support structure 20 may be movable as a single unit, for example the support structure 20, including all of the plurality of sections 20a, 20b, 20c, 20d may be movable as a single unit, e.g., the support structure 20 may be raised or lowered as a single unit, for example using the bed support 12. The support structure 20 may be rotatable as a single unit about the central pivot point 25, for example all of the plurality of sections 20a, 20b, 20c, 20d may be rotatable as a single unit about the central pivot point 25. The support structure 20 may be configured to support the entire body of a human, for example an adult human from head to toe. The support structure 20 may, therefore, have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure. The support structure 20 may extend along the entire length of the bed 10.

The support structure 20 may have a width equal to or greater than about 0.8 m, 0.9 m, about 1 m or about 1.1 m. The width may correspond to a direction perpendicular or transverse to the length.

The support structure 20 may be raised from the ground by a height of between about 0.1-1 m, about 0.2-0.9 m, about 0.3-0.9 m, or about 0.5-0.9 m The bed 10 may be adjustable such that a concave profile 30 (e.g., a pit or valley) may be created at a region of the bed, for example the third section 20c as described above, and/or a region of the bed 10 where a patient's buttocks rest, in use. This may be a central portion of the bed 10, although could be located slightly off centre. The central portion may be defined as being a position along the length of the bed 10 which is a distance that is about 0.35-0.65 times the length of the bed 10 or support structure 20 as measured from either the upper end 14 or the lower end 16 of the bed 10 or support structure 20.

For example, the concave profile 30 may be located at a position along the length of the bed which is a distance that is about 0.4-0.5 times the length of the bed 10 or support structure 20 as measured from the lower end 16 of the bed 10 or support structure 20.

A point of inflection 32 of the concave profile 30 may be located in this region, and in some embodiments the point of inflection 32 may be located at a position along the length of the bed which is a distance that is about 0.45 times the length of the bed 10 or support structure 20 as measured from the lower end 16 of the bed 10 or support structure 20.

The length of the bed 10 may be taken as the length of the support structure 20, for example made up of the lengths of each of the sections 20a, 20b, 20c, 20d of the support structure 20.

The concave profile 30 may be created by rotating two sections of the bed (e.g., the upper and lower halves of the third section 20c) such that a concavity or an obtuse angle is formed between the two sections. In the illustrated embodiment of FIG. 1, for example, a concave profile 30 is created by rotating the upper and lower halves of the third section 20c of the support structure 20 accordingly, such that a concavity or an obtuse angle is formed between them.

The concave profile 30 can prevent a patient slipping down the bed 10 in use, in that one of the sections forming the concave profile 30 (e.g., the third section 20c) may resist the movement of a patient in a certain direction. The concave profile 30 may be formed as a result of a corrective action being issued by the control system of the bed.

In some embodiments one or more sections of the support structure 20 may be configured to support the legs (e.g., the lower half of the third section 20c and/or fourth section 20d in FIG. 1), for example the upper legs. This section may be configured such that it can be rotated above the horizontal (e.g., a horizontal line parallel with the ground) in order to resist the movement of a patient, for example movement towards the lower end 16 of the bed 10. This can be helpful in preventing slippage of the patient, for example when the patient raises the sections of the bed supporting the back and/or head (e.g., the first section 20a and/or the second section 20b), e.g., when sitting up.

As described above and in reference to the example of FIG. 1, the support structure 20 may comprise two (or at least two) pivot points 24, 26, corresponding to two points of flexure of a human while lying down, namely at the knees and waist. A further pivot point 22 may be provided corresponding to a third point of flexure, for example the neck. Each of the plurality of sections 20a, 20b, 20c, 20d of the support structure 20 may be configured to rotate about a pivot point 22, 24, 25, 26.

A first 22 of the pivot points may be located approximately at the location a patient's neck or shoulders rest on the bed 10, for example a position along the length of the bed 10 which is a distance that is about 0.10-0.35, about 0.10-0.25, about 0.10-0.20, about 0.10-0.15 or about 0.125 times the length of the bed 10 or support structure 20 as measured from the upper end 14 of the bed 10 or support structure 20.

A second 24 of the pivot points may be located approximately at the location a patient's waist rests on the bed 10, for example a position along the length of the bed 10 which is a distance that is about 0.35-0.65, about 0.35-0.55, about 0.40-0.45 or about 0.425 times the length of the bed 10 or support structure 20 as measured from the upper end 14 of the bed 10 or support structure 20.

A third 26 of the pivot points may be located approximately at the location a patient's knees rest on the bed 10, for example a position along the length of the bed 10 which is a distance that is about 0.65-0.90, about 0.75-0.90, about 0.80-0.90, about 0.85-0.90 or about 0.875 times the length of the bed 10 or support structure 20 as measured from the upper end 16 of the bed 10 or support structure 20.

It will be appreciated that these dimensions could vary in the disclosed ranges due to the shape of the bed 10 or support structure 20. It is assumed that the bed 10 and/or support structure 20 roughly match the length of a human body, with possibly a gap at the top and bottom to take account of the varying size of different people. The length of the bed 10 or support structure 20 may be the lengthwise or longest dimension of the bed 10 or support structure 20.

The pivot points 22, 24, 25, 26 may be lateral pivot points and the axis of rotation of the pivot points (and the respective sections that rotate about the pivot points) may be transverse to the lengthwise dimension of the bed 10.

Further movement of the bed 10 about other axes of rotation are envisaged within the broadest aspects of this invention.

For example, one or more of the sections 20a, 20b, 20c, 20d may be additionally rotatable about one or more axes of rotation that are not transverse to the longitudinal direction of the bed 10 (i.e., an axis of rotation having a longitudinal component), for example an axis of rotation that is at an angle with respect to the transverse direction, wherein the angle may be selected from the group consisting of: (i) 0°-10°; (ii) 10°-20°; (iii) 20°-30°; (iv) 30°-40°; (v) 40°-50°; (vi) 50°-60°; (vii) 60°-70° (viii) 70°-80°; and (iv) 80°-90°. The one or more additional axes of rotation may be substantially in line with the longitudinal direction, or normal to the transverse direction.

The one or more additional axes of rotation may be provided, for example, so that the patient can perform movements that are not possible by rotating the bed around a transverse axis of rotation.

The support structure 20 may be configured to rotate a single limb or body part of a patient, whilst optionally keeping the remaining limbs or body parts substantially stationary. For example, the support structure 20 may be configured to raise a shoulder independently of the other shoulder, so as to perform a twisting motion of the body. Such an exercise can aid in recovery of a specific injury to one shoulder, for example.

In order to do this the first section 20a and/or the second section 20b of the support structure 20 may be rotatable about an axis of rotation having a longitudinal component, for example an axis of rotation that is at an angle with respect to the transverse direction, wherein the angle may be selected from the group consisting of: (i) 0°-10°; (ii) 10°-20°; (iii) 20°-30°; (iv) 30°-40°; (v) 40°-50°; (vi) 50°-60°; (vii) 60°-70° (viii) 70°-80°; and (iv) 80°-90°.

Such a movement may be effectuated using an additional hinge located at the second transverse pivot point 22, for example, that allows part of the first section 20a and/or the second section 20b to rotate about the axis of rotation having a longitudinal component.

One or more of the sections 20a, 20b, 20c, 20d may be split longitudinally into two sub-sections, for example along a line that is approximately coaxial with a central, longitudinal axis of the bed 10. Each of the sub-sections may be rotatable with the transverse rotation of the section as a whole, but also independently rotatable about a different axis of rotation, for example about an axis of rotation having a longitudinal component, for example an axis of rotation that is at an angle with respect to the transverse direction, wherein the angle may be selected from the group consisting of: (i) 0°-10°; (ii) 10°-20°; (iii) 20°-30°; (iv) 30°-40°; (v) 40°-50°; (vi) 50°-60°; (vii) 60°-70° (viii) 70°-80°; and (iv) 80°-90°. The axis of rotation of the sub-sections may be approximately normal to the transverse axis of rotation.

The independent rotation of the sub-sections may be achieved through the use of one or more hinges located at the pivot point(s) of the support structure 20, or any other suitable mechanism.

In various embodiments, the support structure 20 may comprise a plurality of sections (e.g., at least three sections and/or similar to the sections 20a, 20b, 20c, 20d), and all or part of the sections may be movable by a translating means, e.g., other than rotation about a pivot point. For example, each section may be movable (e.g., up and down) independently of the other sections. Additionally, or alternatively, a portion of each section may be movable (e.g., up and down) independently of the rest of the section, and/or independently of the other sections.

The support structure 20 may comprise or form part of a mattress upon which a patient rests in use. Alternatively a mattress may be separate to the support structure 20 and attached to or rested on the support structure 20.

The Mattress

As discussed above the bed may comprise a mattress and the mattress may form part of the support structure (e.g., be integrated into the support structure) or the mattress may rest on top of the support structure and may further be attached or connected thereto to prevent the mattress moving (e.g., slipping) relative to the support structure.

An example of an integrated mattress and support structure 120 will now be described with reference to FIGS. 2A-2B.

The support structure 120 may form part of a bed 100 and is similar to that shown and described above in respect of FIG. 1. The support structure 120 comprises a plurality of sections 120a, 120b, 120c each configured to support a respective part of a patient's body. In the illustrated embodiment of FIG. 2A a first section 120a is configured to support a patient's upper body, including the back and head, a second section 120b is configured to support a patient's upper legs, and a third section 120c is configured to support a patient's lower legs.

The first section 120a may have a length of between about 0.7-1.1 m, optionally about 0.8 m. The second section 120b may have a length of between about 0.4-0.5 m, optionally about 0.45 m. The third section 120c may have a length of between about 0.5-0.6 m, optionally about 0.55 m. The length may correspond to the lengthwise or longest dimension of the support structure 120. The support structure 120 may extend along the entire length of the bed 100.

As with the embodiment of FIG. 1, each section may be separated from an adjacent section by a transverse separation line (e.g., a pivot point) 122, 124. A first separation line 122 may separate the first section 120a from the second section 120b, and a second separation line 124 may separate the second section 120b from the third section 120c. The first and second separation lines 122, 124 may correspond to the major points of flexure of a human, as discussed above, namely the knees and waist. A crossbeam or lateral support bar may be located at each of the first and second separation lines 122, 124.

A central pivot point 126 may be located at approximately the centre of the bed 10, for example at the point at which a bed support 112 meets the support structure 120, such that the support structure 20 of the bed 10 can rotate as a whole about the central pivot point 126. The central pivot point 126 may not necessarily be located at a point of flexure, and/or may be located at a point between the first and second separation lines 122, 124.

The support structure 120 may have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure. The support structure 120 may extend along the entire length of the bed 100.

The support structure 120 may have a width equal to or greater than about 0.8 m, 0.9 m, about 1 m or about 1.1 m. The width may correspond to a direction perpendicular or transverse to the length.

The support structure 120 may be raised from the ground by a height of between about 0.1-1 m, about 0.2-0.9 m, about 0.3-0.9 m, or about 0.5-0.9 m.

The mattress may comprise a plurality of resilient members 150, for example springs that may extend in the longitudinal (i.e., lengthwise or longest) direction from an upper end 114 of the support structure 120 to a lower end 116 of the support structure 120. The resilient members 150 may be held in place at (e.g., attached to) the upper end 114 by an upper holding member 152, and at the lower end 116 by a lower holding member 154. For example, the resilient members 150 may be attached or connected (e.g., welded) to the upper and lower holding members 152, 154.

The resilient members 150 may be attached to further holding members 156 at each separation line. For example, the resilient members 150 may be attached or connected (e.g., welded) to the further holding members 156, for example to the crossbeams or lateral support bars that are located there (if provided).

The resilient members 150 may be configured to support a patient lying on the support structure 120 and/or may provide the primary support for a patient. While it is envisaged that a further material (e.g., foam or memory foam, which is not shown in FIGS. 2A-2B) may encase the resilient members 150, the shape and/or profile of the mattress may be determined by the shape and/or profile of the resilient members 150, as shown in more detail in FIG. 2B.

The various sections of the support structure 120 may be independently movable (e.g., up and down) and/or rotatable about their respective separation lines 122, 124. As the various sections of the support structure 120 rotate the resilient members 150 may be configured to change shape. In other words, the resilient members 150 may be biased so as to form a predefined shape and/or profile upon rotation of the various sections of the support structure 120. The shape and/or profile of the resilient members 150 (and therefore the mattress) may be different in each section.

Figure 2B:
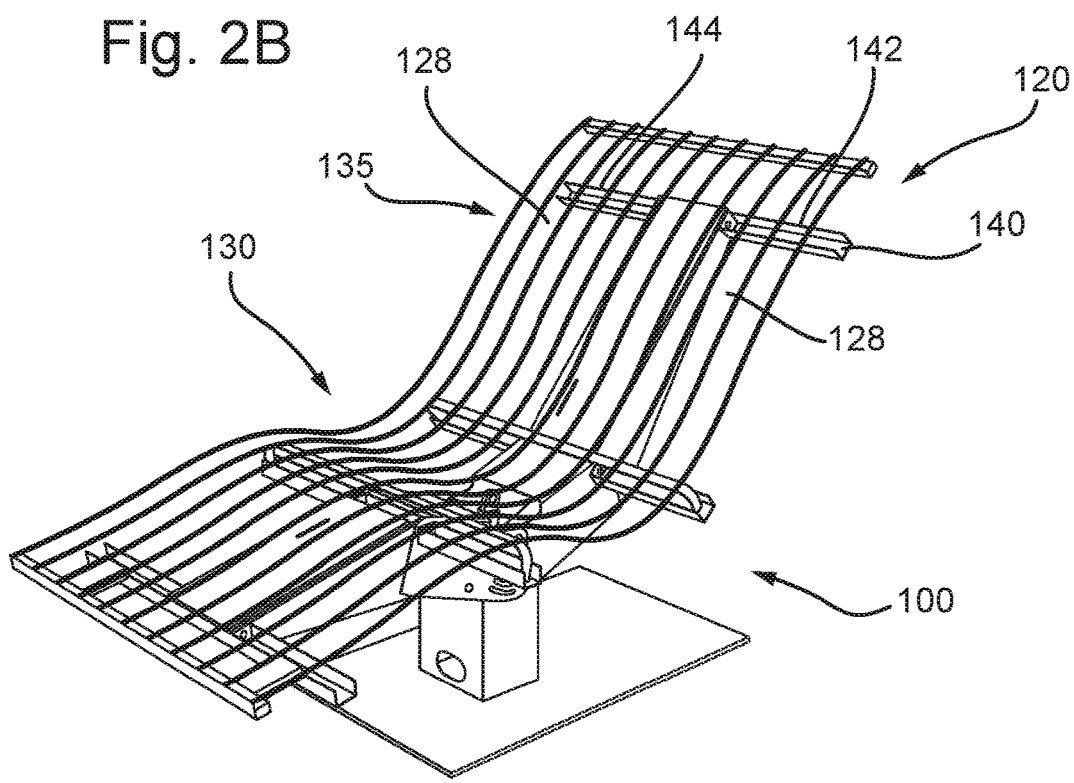

As shown in the illustrated embodiment of FIG. 2B, upon rotation of the first section 120a about the first separation line 122, and/or the third section 120c about the second separation line 124, the resilient members 150 may be configured to form a convex profile in the first section 120a and/or the third section 120c respectively, and may be configured to form a concave profile in the second section 120b.

References to "concave" and "convex" as used herein should be interpreted as being towards a person (e.g., patient) lying on the bed and in the longitudinal direction, for example such that a concave profile forms a depressed portion (e.g., a dip or valley) of the bed in a longitudinal direction, and a convex profile forms a raised portion (e.g., a bump or protrusion) of the bed in a longitudinal direction.

For example, upon rotation of the sections 120a and 120b from a flat position (as shown in FIG. 2A) into a more upright position (as shown in FIG. 2B) the support structure 120 automatically provides a concave profile 130 (e.g., a pit or valley) as well as a convex profile 135 for lumbar support. The use of longitudinal resilient members 150 (as opposed to vertical springs or lateral members) allows such profiling to be more easily tailored for an intended use of the bed.

The resilient members 150 may be configured, in the flat and upright positions of the support structure 120, to substantially conform to the shape of the body. For example, when the support structure 120 is in a flat position the resilient members 150 may preferably undulate to follow the contour of a body in a lying down position, or less preferably the resilient members 150 may be flat. When the support structure 120 is in an upright position, the support structure 120 may undulate to follow the contour of a body in a seated position. It will be appreciated that the undulations in the resilient members 150 when the support structure 120 is in the seated position may be more pronounced than the undulations in the resilient members 150 when the support structure 120 is in the flat position.

There may be no lateral resilient members or springs provided in the support structure 120.

The resilient members 150 may have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure.

The support structure 120 may comprise at least 5, 10, 15 or 20 resilient members 150 and/or the resilient members may be spaced apart by less than 5, 10, 15 or 20 cm, to provide sufficient support to a person lying on the bed 100.

In various embodiments one or more sensors (not shown) may be connected to one or more (or all of) the resilient members 150, for example to ascertain information about the patient therefrom. For example, the tension or movement in each resilient member 150 could be monitored by a control system using suitable sensors in each resilient member 150 (e.g., motion or movement sensors). If it becomes apparent that the patient is moving towards the side of the bed, for example the tension in a central resilient member is reducing and the tension in an outer resilient member is increasing, the control system may determine that the patient is about to fall off the bed, as discussed above in respect of the monitoring methods. The control system may then be configured to sound an alarm or otherwise alert a caregiver (or other person) prior to the patient actually falling off the bed. In embodiments where the bed comprises one or more movable portions, the control system may move (e.g., raise) a suitable portion of the bed in order to prevent the person falling off. This is an improvement over many conventional arrangements that provide an alert once the patient has fallen off the bed, but not beforehand.

The tension in the resilient members 150 could be monitored over time by the control system. Based on the change in the tension in the resilient members 150 over time the control system may determine movement patterns of the patient, some of which may lead to an alert. For example, if the tension is substantially stable then the control system may determine that the patient is moving normally and continue monitoring. If the tension varies by more than a predetermined amount (e.g., due to the patient thrashing or writhing) then the control system could sound an alarm or otherwise alert a caregiver (or other person). The use of sensors connected to the springs of the support structure 120 is seen as an improvement over conventional methods, in that it can more accurately track the movement of the patient. For example, the springs may extend along the entire length of the bed and can, therefore, sense an increased amount of movement of the person on the bed.

The sensors could form an array of sensors, wherein each resilient member 150 comprises a plurality of (e.g., at least 2, 3, 4, 5, 10 or 20) sensors located at regular intervals along the length of each resilient member 150.

Various parts of the support structure 120 may be movable or rotatable in order to provide further automated movement possibilities for a patient, in addition to the rotation about the first and second separation lines 122, 124, and/or the central pivot point 126, and such movements can form part of a corrective action as discussed above.

For example, the upper corners 128 of the support structure 120 may be adjustable such that they can be raised or lowered independently of each other and/or the other parts of the support structure 120. This can provide a movement configured to lift the shoulder of a patient lying on the bed, and can form part of a corrective action as discussed above.

To effectuate such movement a support bar 140 may be located at or near the upper end 114 of the support structure 120. The support bar 140 may comprise a left arm 142 and a right arm 144, both of which may be independently raised or lowered. One or more motors (not shown) may be provided to raise and lower each of the left arm 142 and right arm 144.

A similar arrangement may be placed at the lower end 116 of the support structure 120 in order to raise and lower the legs or feet of a patient lying on the bed.

Other movements are envisaged. The support structure 120 may be configured such that it can be raised and/or lowered about a longitudinal axis of rotation, for example the central longitudinal axis of the support structure 120. For example, each separation line may comprise a support bar similar to the support bar 140, wherein the support bars may be configured to simultaneously raise all of the right or left arms, so that one half of the support structure 120 is raised. Such a movement may assist in turning a patient, which could form part of a corrective action.

In various embodiments, the support structure 120 may comprise a plurality of sections (e.g., at least three sections and/or similar to the sections 120a, 120b, 120c), and all or part of the sections may be movable by a translating means, e.g., other than rotation about a pivot point. For example, each section may be movable (e.g., up and down) independently of the other sections. Additionally, or alternatively, a portion of each section may be movable (e.g., up and down) independently of the rest of the section, and/or independently of the other sections.

The portion of each section may be independently movable by configuring the resilient members 150 such that each resilient member 150 is independently movable within that portion of the section. For example, separate actuators could be provided for each resilient member 150 that may be configured to move the resilient member 150 up and down within a particular section, or within a portion of a particular section.

Amplified or Assisted Movement

A further aspect of the present invention will now be described, and can be combined with any of the aspects or embodiments of a bed disclosed herein.

A method is disclosed that comprises providing a bed upon which a human or animal lies, in use, for example a medical (e.g., hospital) bed. The bed may be separated into one or more portions that each correspond to a specific part of the body, for example a limb such as a leg or arm, a shoulder, the torso or lower body, etc. The bed may be a bed as shown and described above in respect of FIG. 1, or FIGS. 2A-2B.

The bed may be configured such that each of the portions may be movable, so that the part of the body corresponding to each portion can be moved in a specified direction, for example to allow a patient lying on the bed to sit up, or perform an exercise such as a shoulder movement or leg raise. In various embodiments the movement may be to alleviate bedsores, and could form part of a corrective action that is intended to alleviate bedsores once they have been determined to exist (e.g., by the assessment module).

A control system may be provided and may be configured to move the portion of the bed in its specified direction if and/or when the specific part of the body corresponding to that portion is moved.

Additionally, or alternatively, the control system may be configured to amplify the movement of a part of the body by moving the portion of the bed corresponding to that part of the body in its specified direction, for example after detecting movement of that part of the body, which movement may be in the specified direction.

This is in contrast to conventional arrangements, which typically employ a control panel (or similar) in order to move a part of the body (e.g., sit up), but do not effectuate movement of the bed in response to movement of the patient. The principle of this aspect of the invention is that the bed should amplify, rather than initiate the movement of a patient.

It will be appreciated that not all movements of a patient would want to be amplified, or indeed that amplification, as opposed to initiation of movement is desired all the time. The control system may be switchable such that a patient or caregiver can turn on and off the function of amplified movement. For example, if a patient wants to sit up, but is not fit or well enough to use the amplified movement then the control system may be switched off. The patient can then use conventional controls to cause the bed to raise the upper body. However, if the patient would like to sit up with the amplified movement, the control system may be switched on. This means that the movement of the patient becomes the cause of the movement of the bed.

The control system may only effectuate movement of the bed after a given period of time has passed since the patient moved the body part in question. This can be made short enough to prevent unwanted fatigue, but long enough to prevent unnecessary or undesired movement of the bed, for example in response to a spasm. This function may not always be necessary, for example for certain movements or if the control system is switchable as described above.

The control system may include a switch configured such that the amplified movement can only be activated by the control system if the switch is depressed or otherwise activated. For example, a button may be provided on the bed, and the control system may only carry out the amplified movement if the button is depressed. Other types of switch may be used, such as a voice activated switch, or a switch that is controlled by a specific movement (e.g., an arm motion or eye movement). This would help avoid unwanted movements, and could be used in addition, or alternatively to the other methods of avoiding unwanted movements described herein.

Varying degrees of assistance may be provided. It is recognised that some patients may need more assistance than others. The control system may include one or more assistance factors that can be set by a user (e.g., the patient or a nurse/caregiver). The assistance factors may range from, e.g., 0-1, where 0 corresponds to no or minimum assistance and 1 corresponds to full or maximum assistance. The factor may increase from 0-1, for example in a linear fashion.

The control system may vary the power used to move the portion of the bed in its specified direction based on (e.g., in proportion to) one of the assistance factors, for example the higher the assistance factor the more power may be applied to move the portion of the bed, and vice-versa.

The control system may also vary the response time of the movement based on one of the assistance factors. The response time may refer to the time taken for the control system to effectuate movement of the portion of the bed in question, once the patient starts to move or initiates a movement. For a high assistance factor the control system may use or apply a shorter response time, and for a low assistance factor the control system may use or apply a longer response time.

It will also be appreciated that certain exercises may be possible. The control system may store a routine (e.g., in a memory device) and this may correspond to the part of the body corresponding to the portion of the bed in question, for example a leg. The control system may be configured to amplify the movement of the body part (e.g., leg) once it starts to move. The control system may be configured to do this for a set number of repetitions, and/or for multiple body parts (and multiple corresponding portions of the bed, such as each leg, or upper body and lower body, consecutively.

The one or more portions of the bed may correspond to portions of the bed that are configured to support certain parts of a patient's body in use. As discussed above the bed may be a bed as shown and described above in respect of FIG. 1, or FIGS. 2A-2B, in which case each portion of the bed may correspond to a section or sub-section of the bed or support structure as described above, wherein movement of the portions may be effectuated in the same manner as described above.

One or more motors may be provided to move the portions of the bed in the specified directions, which motors may be controlled by the control system. The control system may comprise a memory and a processor, wherein the memory stores data relating to the movements of the bed and the processor is configured to carry out the control steps described above in relation to the control system.

The portions of the bed may overlap one another. For example, first and second portions of the bed may be configured to support the upper and lower body of a patient lying on the bed, respectively. A third portion of the bed may be configured to support a right shoulder or arm of the patient, and a fourth portion of the bed may be configured to support a left shoulder or arm of the patient. The third and fourth portions may, therefore, be located within (and may form part or all of) the first portion. A similar arrangement may be created in the second portion by dividing this into fifth and sixth portions. Thus, the bed may be divided into quadrants, where the upper and lower halves of the bed may be movable as well as each quadrant.

Each portion of the bed may be independently movable, for example using one or more motors (not shown). Each portion of the bed may have a dedicated motor, or one or more switches may be configured to switch the transmission of one of the motors from one portion of the bed to another.

In an additional, related aspect a method is disclosed that comprises providing a bed upon which a person lies, for example a medical (e.g., hospital) bed. The bed may be separated into one or more portions that each correspond to a specific part of the body, for example a limb such as a leg or arm, a shoulder, the torso or lower body, etc.

The bed may be configured such that each of the portions may be movable, so that the part of the body corresponding to each portion can be moved in a specified direction, for example to allow a patient lying on the bed to sit up, or perform an exercise such as a shoulder movement or leg raise.

A control system may be configured to store a routine (e.g., in a memory device) and this may correspond to the part of the body corresponding to the portion of the bed in question, for example a leg. The control system may be configured to move the portion of the bed in question (e.g., raise and lower the portion) a certain number of repetitions. The number of repetitions may be stored in a memory of the control system, and/or may predetermined or set by a user (e.g., a caregiver).

The bed may be similar to the bed described above in respect of the amplified movement, although this aspect of the invention is related to the use of a moving bed that is divided into portions to provide dedicated and/or focused exercises, rather than amplified movement.

Instead of (or additionally to) the control system being configured to store a routine, the control system may be configured to move one or more of the portions of the bed in its specified direction if and/or when a bedsore is detected.

The bedsore may be detected through the use of one or more sensors at each portion, which sensors may be configured to detect pressure caused by the patient lying in one position for an extended period of time. For example, the sensor may be configured to detect when a patient has not moved a particular part of their body (and/or their body as a whole) for a period of time, and notify the control system accordingly.

One or more pressure sensors may be configured to sense the pressure at a particular location on the bed. There may be an array of pressure sensors configured in this manner. Each pressure sensor may be configured to send pressure data to the sensor analysis module, which may analyse the pressure data and output a patient feature therefrom. For example, if a particular pressure sensor detects a pressure above a threshold and for a sustained period of time, the sensor analysis module may output a patient feature (e.g., a notification) that a sustained pressure has been detected at the portion of the bed corresponding to the particular pressure sensor. This patient feature may be received by the assessment module, which may determine that a bedsore is present in that portion of the bed (e.g., if the patient also has not moved within the same timeframe).

In response, as a corrective action the control system may move a selected portion or portions of the bed in its or their specified direction to alleviate the bedsore. The portion or portions moved may correspond to portions of the bed in which the most pressure was applied by the patient's body during the period of time, or other portions of the bed. The period of time may be a period longer than 30, 60, 120, 240 or 480 minutes.

The control system (e.g., the assessment or action module) may store data (e.g., in memory), including instructions for the control system to move a predetermined portion or portions of the bed in response to a bedsore being detected. This may depend on the type and/or location of the bedsore, for example a bedsore detected in a portion of the bed corresponding to the left leg may be alleviated by raising that portion of the bed. Alternatively, a bedsore detected in the lower back may be alleviated by raising the portion of the bed corresponding to both legs.

Again, the bed may be similar to the bed described above in respect of the amplified movement and/or to provide dedicated and/or focused exercises.

References to "concave" and "convex" as used herein should be interpreted as being towards a person (e.g., patient) lying on the bed and in the longitudinal direction, for example such that a concave profile forms a depressed portion (e.g., a dip or valley) of the bed in the longitudinal direction, and a convex profile forms a raised portion (e.g., a bump or protrusion) of the bed in the longitudinal direction.

Although the present invention has been described with reference to preferred embodiments, it will be understood by those skilled in the art that various changes in form and detail may be made without departing from the scope of the invention as set forth in the accompanying claims.

The invention claimed is:

1. A support and monitoring system for a human or animal comprising:
    a support structure comprising a plurality of resilient members, each resilient member extending in a longitudinal direction from an upper section of the support structure to a lower section of the support structure, and each resilient member is spaced apart from an adjacent resilient member in a transverse direction, and
    a monitoring system for said support structure, the monitoring system comprising:
        a plurality of sensors configured to monitor a tension or movement of each resilient member, and
        a processor or circuitry configured to monitor the tension or movement of each resilient member over time using the plurality of sensors,
    wherein the monitoring system is configured to determine if the person or animal on the support structure is moving laterally towards a side of the support structure based on the tension or movement of each resilient member, and once it is determined that the person or animal on the support structure is moving laterally towards the side of the support structure, the processor or circuitry is configured to cause a movement of the plurality of resilient members.

2. The system of claim 1, wherein each of the plurality of sensors is connected to a respective one of the plurality of resilient members.

3. The system of claim 1, wherein the processor or circuitry is configured to determine if the person or animal on the support structure is moving laterally towards the side of the support structure based on a determination that a tension or movement of a central resilient member is decreasing while a tension or movement of an outer resilient member is increasing.

4. The system of claim 1, wherein once it is determined that the person or animal on the support structure is moving laterally towards the side of the support structure, the processor or circuitry is configured to sound an alarm or other alert.

5. The system of claim 1, wherein the movement causes the support structure to form a concave profile.

6. The system of claim 5, wherein the plurality of resilient members comprises at least 5 resilient members located in a parallel array across the support structure, wherein the plurality of resilient members provide a primary support for the person or animal on the support structure.

7. The system of claim 6, wherein the support structure forms part of a bed and the monitoring system is configured to monitor the person or animal on the bed.

8. The system of claim 1, wherein the plurality of resilient members comprises at least 5 resilient members located in a parallel array across the support structure.

9. The system of claim 1, wherein the plurality of resilient members provide a primary support for a person or animal on the support structure.

10. The system of claim 1, wherein the support structure forms part of a bed and the monitoring system is configured to monitor a person or animal resting on the bed.

11. A support and monitoring system for a human or animal comprising:
    a support structure comprising a plurality of resilient members, each resilient member extending in a longitudinal direction from an upper section of the support structure to a lower section of the support structure, and each resilient member is spaced apart from an adjacent resilient member in a transverse direction, and
    a monitoring system for said support structure, the monitoring system comprising:
        a plurality of sensors configured to monitor a tension or movement of each resilient member, and
        a processor or circuitry configured to monitor the tension or movement of each resilient member over time using the plurality of sensors, and determine one or more movement patterns of a person or animal on the support structure based on a change in the tension or movement of each resilient member,
    wherein the processor or circuitry is configured to determine that the person or animal is moving normally if the tension or movement in the plurality of resilient members does not vary by more than a predetermined amount, and determine that the person or animal is moving abnormally if the tension or movement in the plurality of resilient members varies by more than the predetermined amount.

12. The system of claim 11, wherein the processor or circuitry is configured to perform analysis of the one or more movement patterns and determine a health assessment therefrom.

13. The system of claim 12, wherein the processor or circuitry is configured to perform analysis of at least a first patient feature and a second patient feature to produce a combined analysis, and to determine the health assessment based on the combined analysis, wherein the first patient feature includes the one or more movement patterns.

14. The system of claim 13, wherein the other patient features have been determined from analysing one or more sensory outputs associated with the support structure.

15. The system of claim 14, wherein the plurality of resilient members comprises at least 5 resilient members located in a parallel array across the support structure, wherein the plurality of resilient members provide a primary support for the person or animal on the support structure.

16. The system of claim 11, wherein each of the plurality of sensors is connected to a respective one of the plurality of resilient members.

17. The system of claim 11, wherein the plurality of resilient members comprises at least 5 resilient members located in a parallel array across the support structure.

18. The system of claim 11, wherein the plurality of resilient members provide a primary support for a person or animal on the support structure.

19. The system of claim 11, wherein the support structure forms part of a bed and the monitoring system is configured to monitor a person or animal resting on the bed.

* * * * *